United States Patent [19]

Raines

[11] Patent Number: 4,535,820

[45] Date of Patent: Aug. 20, 1985

[54] NORMALLY CLOSED CHECK VALVE

[75] Inventor: Kenneth C. Raines, Bethlehem, Pa.

[73] Assignee: Burron Medical Inc., Bethlehem, Pa.

[21] Appl. No.: 613,644

[22] Filed: May 24, 1984

[51] Int. Cl.³ .............................................. F16K 15/14
[52] U.S. Cl. ..................................................... 137/854
[58] Field of Search ............... 137/843, 851, 852, 854, 137/515, 798

[56] References Cited

U.S. PATENT DOCUMENTS

| | | | |
|---|---|---|---|
| 4,181,146 | 1/1980 | Goglio | 137/854 |
| 4,210,173 | 7/1980 | Choksi et al. | 137/843 |
| 4,222,407 | 9/1980 | Ruschke et al. | 137/512.15 |
| 4,246,932 | 1/1981 | Raines | 137/512 |
| 4,286,628 | 9/1981 | Paradis et al. | 137/843 |
| 4,310,017 | 1/1982 | Raines | 137/533 |
| 4,369,812 | 1/1983 | Paradis et al. | 137/843 |
| 4,434,811 | 3/1984 | Murdoch | 137/515 |

*Primary Examiner*—Martin P. Schwadron
*Assistant Examiner*—Sheri Novack
*Attorney, Agent, or Firm*—Shoemaker and Mattare, Ltd.

[57] ABSTRACT

A normally closed, one-way check valve having a body composed of two cylindrical containers which complement each other, each of said containers having a tubular projection with a liquid opening therethrough, one of said cylindrical chambers provided with a plurality of longitudinally extending ribs therealong for preventing sticking of a valve disc as contained within an assembled valve device, also further including a traverse bar for pressing against a valve disc. The other body component is provided with a pointed triangular support and also a plurality of radially extending ribs for preventing a valve disc from opening so far as to close off the egress port provided with said second element, together with a rubber resilient valve disc which is retained between the pointed triangular support and the traverse bar when the unit is assembled by sonic welding into a permanently assembled device. A further embodiment provides for a permanent dimple in the valve disc prior to assembly of the component elements, while a further embodiment provides a valve disc with an elongated groove or recess of somewhat oval shape for reception of the pointed triangular support member of the second body component.

17 Claims, 5 Drawing Figures

U.S. Patent  Aug. 20, 1985  4,535,820
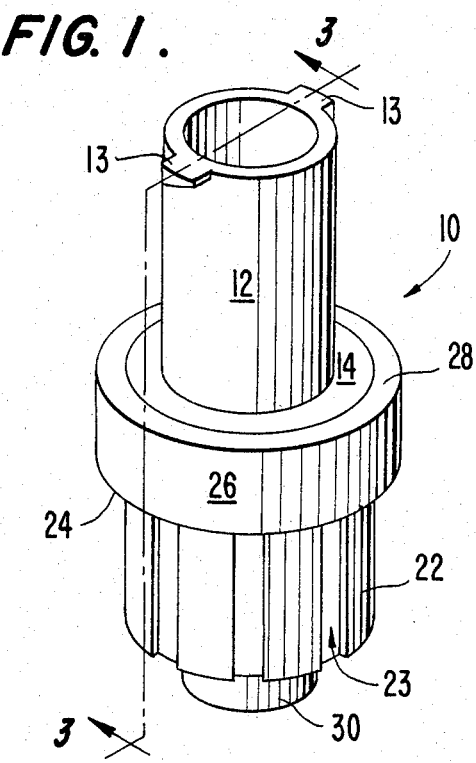
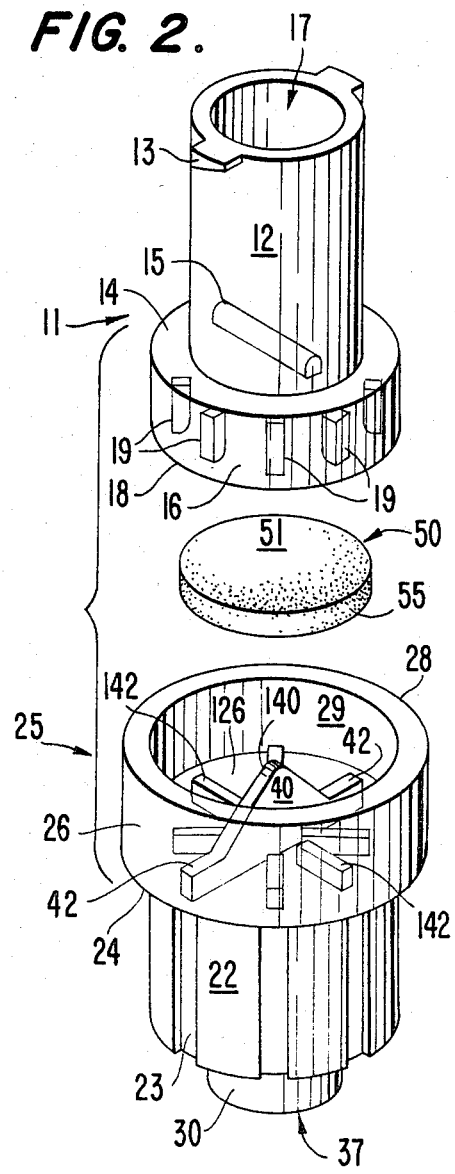
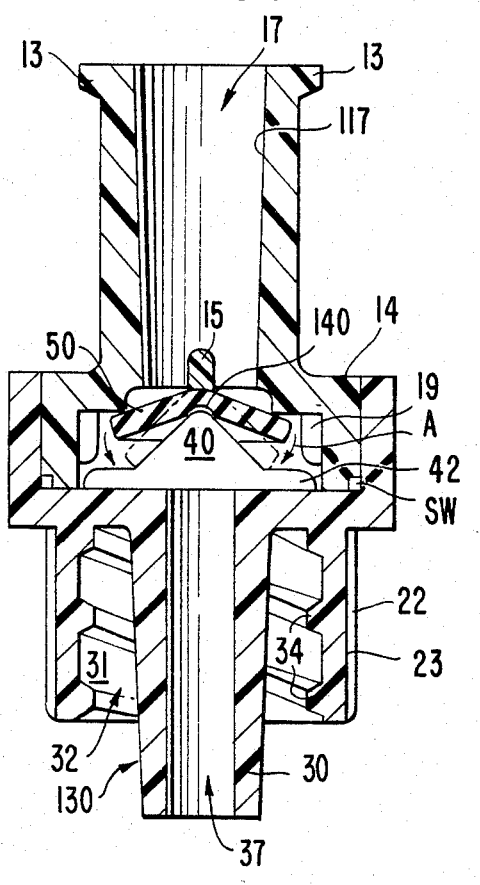
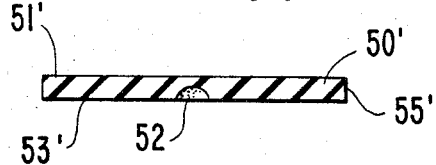
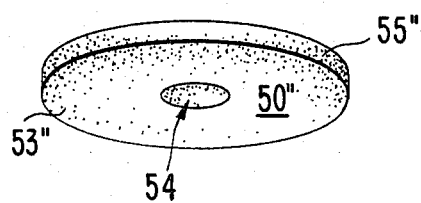

NORMALLY CLOSED CHECK VALVE

BACKGROUND OF THE INVENTION

1. Field of the Invention

This invention relates generally to backflow check valves for use with liquid flow and administration structures for medical purposes.

2. Description of the Prior Art

A common problem of known devices of the conventional type is that upon reversal of liquid flow through tubing from a hypodermic syringe or the like, the known type check valves fail to respond as quickly as desired to the closed position. That it, there is always the risk of backflow from the output to the input, which in many instances if very undesirable, and in some cases, even deadly.

There have been devices made to be normally closed and under stress, whereby the valve in order to remain open must be subject to a high flow pressure, and thus when the flow pressure is decreased, the valve will quickly close. This is a great improvement over the afore-mentioned check valve; however, it still can be improved upon. The disadvantage of this type is that the valve disc itself may tend to move off center and thus have a tendency to bind an edge against one of the peripheries of the enclosing wall.

Existing prior art patents which may be pertinent to the present invention are as follows:

U.S. Pat. No. 4,369,812—1/25/83—Paradis et al.
U.S. Pat. No. 4,310,017—1/12/82—Raines
U.S. Pat. No. 4,286,628—9/1/81—Paradis et al.
U.S. Pat. No. 4,246,932—1/27/81—Raines
U.S. Pat. No. 4,222,407—9/16/80—Ruschke et al.

U.S. Pat. Nos. 4,246,932 and 4,310,017 were both invented by the same inventor as the present one, and both are assigned to the same assignee as the present application. The first patent discloses a flexible disc 150 which rests on a plurality of ribs 166 located about the lower surface of the disc. Disc 150, which is normally closed, folds open under high pressure, and thus permits flow of the desired liquid. However, upon reversal of flow, the disc will promptly close and prevent same. A triangular support 186 holds the mid-portion of the disc against the cross bar 170 (see FIGS. 2, 4 and 5). However, except for the pressure between the point of the triangular support and the bearing surface of the cross bar on opposite sides of the flexible disc 150, there is nothing present to assure that the disc does not move sideways.

The other U.S. Pat. No., 4,310,017, discloses male and female hubs which are sonically welded together with a flow control disc 50 therebetween. However, this device has some of the limitations already stated above.

U.S. Pat. No. 4,222,407 discloses a flexible disc 68 which rests upon a rib 58 which extends entirely across the diameter of the disc. This rib normally holds the disc against the valve seat (surface 20) to thus be normally closed. However, upon pressure flow of fluid, the disc will fold over rib 58 and permit liquid passage thereby. Again, this device does not provide any specific structure for preventing the disc from sideways movement and thus binding of a peripheral edge against an inner sidewall of the chamber of the assembled body.

Both U.S. Pat. Nos. 4,286,628 and 4,369,812 are to Paradis et al., and disclose other check valve structure involving movable discs therewith. A two-part body is assembled to contain a flexible control disc therebetween. Longitudinal channels 26 are provided at the periphery of control channel 21 to facilitate reverse flow through the valve. However, structure like that disclosed in the present invention for preventing binding or off center movement of the valve disc is not disclosed.

None of the known prior art devices offer the new and novel features of the present invention.

SUMMARY OF THE INVENTION

An object of the present invention is to provide a normally closed, high pressure check valve for use with administration of fluids and medicinal liquids in medical environments.

Another object of the present invention is to provide a one-way check valve structure including a flexible resilient disc which is maintained centered within the working body of the device, and prevented from movement off center of a central axis thereof, and/or frictional restraint or binding of a peripheral edge of the disc.

A further object of the present invention is to provide a high pressure check valve, which is normally closed, which can very quickly open and just as quickly close to prevent backflow of liquid being administered, and which has specific structure for preventing movement of the disc offcenter of the valve body and resultant impedement of the quick acting movement of the peripheral edges of the valve disc.

A still further object of the present invention is for a one-way check valve which is very quick acting, and structurally arranged so that no interference can occur through side movement of the valve disc within the valve body. A dimple or elongated recess in conjunction with a pointed triangular support effectively maintains the centered position of the valve disc within the valve body. In addition, longitudinally extending ribs within the inner circumference of the valve body permit full flow of liquid around the peripheral edges of the valve disc, but assure that the peripheral edge will not be restrained in movement by the inner walls of the body.

The present invention provides a number of new and novel features over the check valves presently in use. A two-part body, each having a cylindrical container portion therewith, when assembled restrains a flexible valve disc therewithin. A pointed triangle with one body element supports the central area of the disc, which in turn is under pressure from a traverse bar mounted in the other body element. If the pressure between the triangle point and the bar are sufficient, the flexible disc will be restrained against sideways movement. However, to assure that no such sideways movement can occur, a dimple, or elongated recess or oval groove, can be provided within the surface of the disc which receives or engages with the triangular point. By use of such a recess or groove in one face of the flexible disc, it is positively retained in centered position with respect to the central axis of the valve body.

To further assure that no peripheral edge binding of the flexible disc can occur, longitudinally extending ribs are preferably provided within the inner wall of the body element most closely surrounding the valve disc. Such ribs, being spaced quite far apart and relatively small in width, permit almost as much fluid flow as a valve without such ribs, but greatly increase the assurance of free flexible movement of the valve disc periphery without binding.

These together with other objects and advantages which will become subsequently apparent reside in the details of construction and operation as more fully hereinafter described and claimed, reference being had to the accompanying drawing forming a part hereof, wherein like numerals refer to like parts throughout.

BRIEF DESCRIPTION OF THE DRAWINGS

FIG. 1 is a perspective view of the assembled device of the present invention.

FIG. 2 is an exploded perspective view of the component elements of the present invention as disassembled.

FIG. 3 is a cross-sectional view taken generally along line 3—3 of FIG. 1.

FIG. 4 is a cross-sectional view of a valve disc per se having a restraining dimple in the middle portion thereof.

FIG. 5 is a perspective view of another embodiment of the valve disc as provided with a centering and restraining oval/elongated recess in one surface thereof.

DETAILED DESCRIPTION OF THE PREFERRED EMBODIMENTS

Referring to FIG. 1 of the drawing, reference numeral 10 indicates in general the present invention. The one-way, normally closed check valve of the present invention includes a valve body made of two component body elements. One element 11 has a tubular portion 12 terminating in an enlarged container 16. Locking ears 13 are provided at one end of tubular portion 12, while the container portion 16 at the other end has an upper surface or shoulder 14 and an outer or lower surface 18. A traverse cross bar 15 is formed within this element, with the axis thereof being in line with the surface 14. A longitudinal inlet opening, preferably having a female taper 117, extends through tubing 12 into the interior of container 16. The inner circumferential wall of the container 16 is provided with a plurality of longitudinally extending ribs 19. These ribs are for the specific purpose of preventing binding of the peripheral edge of the flexible valve disc as contained within this body portion of the valve after assembly with the other body element thereof.

The other body element 25 for the valve comprises a can 26 having an outer surface 28 and a lower shoulder 24, integral with a double tubular extension 22 and 30, best seen in the cross-sectional view of FIG. 3. Within the outer tubular portion 22 is an inner wall 31 provided with threads 34 for attachment to appropriate flow structure. The central tubular portion 30 is provided with an inner outlet opening 37 therethrough and an outer male lauer taper 130.

Recesses 23 also are provided in the outer circumference of outer tubular portion 22.

The valve disc itself is a circular disc 50 provided with opposite surfaces 51 and 53, both of which are substantially flat.

A triangular pointed member 40 having extending ribs 42 therewith is molded or integrally affixed to the lower body element 26. Additional radial supporting ribs 142 are preferably also integrally formed with this body element. The purpose of ribs 42, 142 is to assure that when the flexible disc is completely open, as indicated by the dotted lines and the flow arrow A in FIG. 3, an adequate space will always remain for liquid flow about the peripheral edge of the disc and above the surface 126 of the larger body element.

After the component elements of FIG. 2 are assembled into position as shown in FIG. 3, sonic welding SW is preferably used to securely fasten the two body components into a single integral unit. Once assembled, the device cannot be again disassembled without complete destruction of the device.

Upon assembly, the lower surface of the traverse bar 15 of the upper (as shown) first body element firmly presses against the mid-portion of the flexible disc and presses same against the upper tip of triangular point 40. Preferably, the pressure is such that the triangular tip will form a small indentation 140 (FIG. 3) within the disc. This indentation 140 then will positively restrain the disc from sideways movement. However, if any sideways movement should occur, or if during assembly the disc happens to move slightly off center so that one peripheral edge tends to engage against the inner circumferential wall of container 16, the longitudinal ribs 19 within container 16 will assure that no frictional binding will take place.

FIG. 4 shows a modified embodiment of the above described invention. In this embodiment, the flexible, resilient, preferably rubber, valve disc 50' has been provided with a permanent dimple 52 at the central axis of the disc. Thus, in the surface 53, which in the first embodiment is perfectly smooth and undeformed until after assembly of the device wherein indentation 140 is made, a recess or dimple is preformed in this embodiment. This assures that the disc will be appropriately centered during assembly, as well as maintained at the desired central position, and without depending entirely upon pressure between the tip of triangular support 40 and the cross bar 15.

In FIG. 5 a further embodiment of the present invention is disclosed. In this embodiment, the flexible valve disc 50" is provided with an oval or elongated recess 54 in the surface 53". This recess better fits the rounded, tapered tip 140 of triangular point 40. Again, this oval recess will restrain the disc against sideways movement and thereby assure that the peripheral circumference or edge 55" will not bind or engage against the inner circumferential wall of the inner body element.

The present invention in all of its embodiments offers a number of important advantages over the known prior art. By positively assuring that the flexible disc is always centered, and cannot move sideways of the body container, positive and efficient one-way check action of the valve device is always assured. While the structural differences over known prior art may seem small, the difference is quite significant in actual practice and use. In the field with which this device is used, just one failure at any time is absolutely one too many.

Actual performance values of the valve are as follows:

Crack Pressure: 1.5 PSI minimum (Pressure required to open valve)

Maximum Injection Pressure: 75 PSI

Flow Rates: 750 ml/minute at 5 PSI 2,250 ml/minute at 30 PSI

The foregoing is considered as illustrative only of the principles of the invention. Further, since numerous modifications and changes will readily occur to those skilled in the art, it is not desired to limit the invention to the exact construction and operation shown and described, and accordingly all suitable modifications and equivalents may be resorted to falling within the scope of the invention.

I Claim:

1. A valve device comprising:
   a first body element having an input opening therethrough;
   a second body element which complements said first body element and having an outlet opening therefrom;
   a resilient valve disc mountable between said first and second body elements;
   first means with one body element for supporting the disc at the center thereof;
   means with the other body element for holding said disc firmly against said first means in such a manner that said disc is restrained from sideways movement; and
   wherein said disc element is round, and both said first and second body elements have round container portions in which said disc element upon mounting is suitably spaced from the edges thereof, and wherein said means for preventing sideways movement of said disc element includes pressure between said two body element means for partially deforming the center area of said disc to restrain same against sideways movement.

2. The valve of claim 1, together with further means for preventing the disc from blocking the path of fluid flow in the open direction thereof.

3. The valve of claim 2, together with additional means for preventing the circumferential edge of the disc from binding or sticking against the sides of the body element it is most closely adjacent to.

4. The valve of claim 3, wherein said means for preventing the disc edge from binding against the sides of the body element comprise ribs which extend lengthwise of the inner circumferential wall of said body element.

5. The valve of claim 2, wherein said further means for preventing the disc from blocking the path of fluid flow include a plurality of radially extending ribs along the floor of the other body element having the outlet opening therethrough.

6. The valve of claim 1, wherein said means with one body element for supporting the disc at the center thereof comprises a pointed triangular member which makes a depression directly in the smooth surface of the flexible rubber valve disc.

7. The valve of claim 6, wherein said valve disc is normally flat on both surfaces and is only deformed at the center thereof under pressure between said first and second means.

8. The valve of claim 6, wherein at least one surface is provided with a dimple for receiving said triangular point of said second body element.

9. The valve of claim 6, wherein at least one surface is provided with an elongated oval recess for receiving said triangular point of said second body element.

10. A normally closed one-way check valve comprising: a first cylindrical chamber having an opening centrally thereof; a second cylindrical chamber having an opening centrally thereof, said first cylindrical chamber having a slightly smaller external diameter than the internal diameter of said second cylindrical chamber so that it complements and fits inside thereof for forming an overall closed chamber body element; one of said cylindrical chambers provided with a traverse bar thereacross; said same cylindrical chamber being provided with a plurality of longitudinal ribs circumferentially around the inner wall of said cylindrical chamber; the other cylindrical chamber provided with a pointed support member together with a plurality of radially ribs; a resilient disc mounted in compression between said pointed support member and said traverse bar in such a manner that a depression is made in the central area of said disc so that said disc is restrained from sideways movement within the valve body element chamber.

11. The normally closed one-way check valve of claim 10, wherein said disc is normally flat on both sides except for the central area which is slightly deformed during assembly of the component elements of the valve device.

12. The normally closed one-way check valve of claim 10, wherein at least one surface of said disc is provided with a permanent dimple for receiving said pointed support member of said second body element.

13. The normally closed one-way check valve of claim 10, wherein at least one surface is provided with an elongated oval recess for receiving said pointed support member of said second body element.

14. The normally closed one-way check valve of claim 10, wherein said opening in said first cylindrical chamber comprises a tubular projection having a female lauer input taper thereto and retainer projections externally thereof.

15. The normally closed one-way check valve of claim 14, wherein said second cylindrical chamber is provided with dual integral tubular projections, one of said integral tubular projections including the central opening therethrough, and the other integral tubular projection being internally threaded for receiving liquid flow structure connected thereto.

16. The normally closed one-way check valve of claim 15, wherein said body component elements are sonically welded together to provide a non-disassembleable valve device.

17. The normally closed one-way check valve of claim 16, wherein said resilient valve disc is made of rubber material.

* * * * *